United States Patent [19]

Sherman

[11] 4,134,940

[45] Jan. 16, 1979

[54] HUMIDIFIER ADAPTER WITH AUDIO RELIEF VALVE

[75] Inventor: Robert M. Sherman, Glenview, Ill.

[73] Assignee: Aerwey Laboratories, Inc., Arlington, Tex.

[21] Appl. No.: 845,407

[22] Filed: Oct. 25, 1977

[51] Int. Cl.² .................. B01F 3/04; A61M 15/00
[52] U.S. Cl. .................... 261/124; 128/186; 128/192; 137/318; 137/846; 261/DIG. 65
[58] Field of Search ............... 261/65, 78 A, 121 R, 261/122-124, DIG. 65; 128/186, 188, 192-194, DIG. 29; 116/70, 114 PV; 137/318, 846, 843, 517, 512.3; 251/340

[56] References Cited

U.S. PATENT DOCUMENTS

| | | | |
|---|---|---|---|
| 711,385 | 10/1902 | Coyle | 116/70 X |
| 1,493,570 | 5/1924 | Slate | 116/70 |
| 1,506,012 | 8/1924 | Lewis | 137/843 |
| 2,709,577 | 5/1955 | Pohndorf et al. | 261/DIG. 65 |
| 3,104,787 | 9/1963 | Thompson, Jr. | 137/846 X |
| 3,196,924 | 7/1965 | Kaminga | 251/340 X |
| 3,351,088 | 11/1967 | Jensen | 137/517 |
| 3,502,097 | 3/1970 | Muller | 137/318 |
| 3,572,660 | 3/1971 | Mahon et al. | 261/78 A |
| 3,633,613 | 1/1972 | Julow | 137/512.3 |
| 3,806,102 | 4/1974 | Valenta et al. | 261/122 X |
| 3,807,445 | 4/1974 | McPhee | 128/188 X |
| 3,870,012 | 3/1975 | Metivier | 128/DIG. 29 |
| 3,910,222 | 10/1975 | Metivier | 116/70 |
| 3,913,843 | 10/1975 | Cambio, Jr. | 261/78 A X |
| 3,978,881 | 9/1976 | Mouranie | 137/318 |
| 4,011,288 | 3/1977 | Assenheimer et al. | 261/DIG. 65 |
| 4,011,828 | 3/1977 | Black | 116/70 |
| 4,036,919 | 7/1977 | Komendowski et al. | 261/122 |
| 4,039,639 | 8/1977 | Kankel et al. | 261/121 R |
| 4,061,698 | 12/1977 | Thornwald | 128/194 X |
| 4,067,414 | 1/1978 | Funke | 137/846 X |

*Primary Examiner*—Richard L. Chiesa
*Attorney, Agent, or Firm*—Fitch, Even, Tabin & Luedeka

[57] ABSTRACT

An adapter for a humidifier is provided that mounts on a sealed container of purified or sterile water and connects usually to a flowmeter which is attached to a pressurized gas container. The adapter includes a spike member to pierce the container wall, a pressure chamber defined between the inner wall of the adapter and the spike member, and port means in the adapter wall establishing communication between the pressure chamber and the outside atmosphere. An audible relief valve means is located in the port to effect audible pressure relief under above normal pressure conditions in the pressure chamber during the humidifying process while pressurized gas is being introduced into the water to moisten the gas.

6 Claims, 5 Drawing Figures

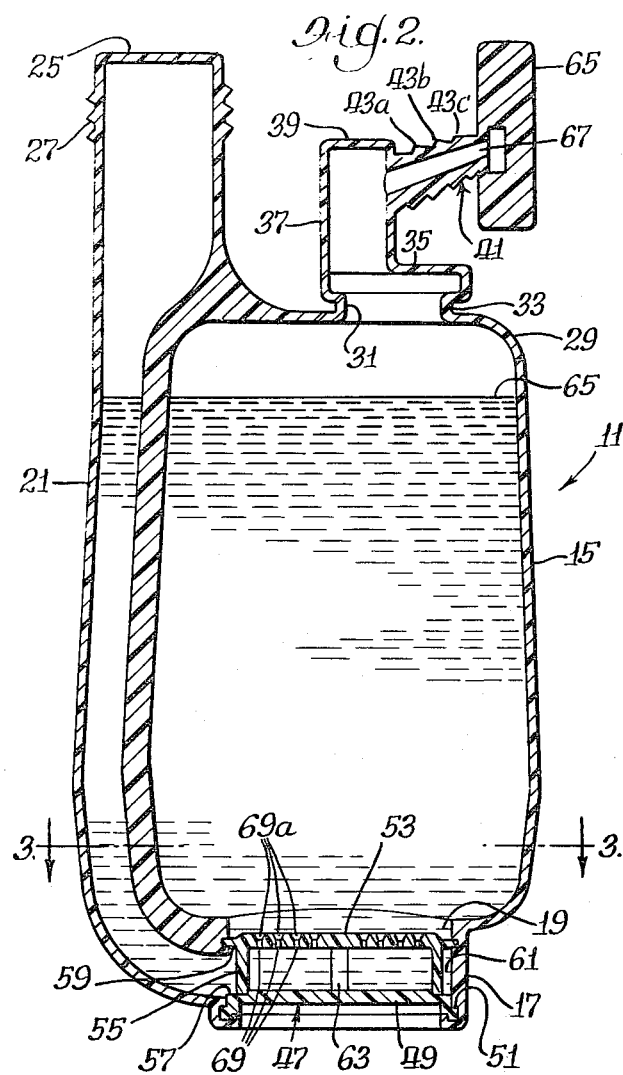
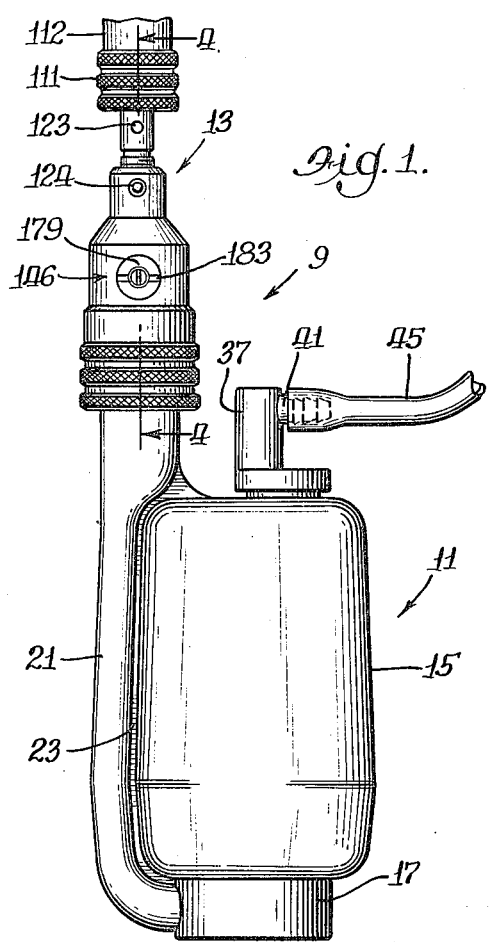
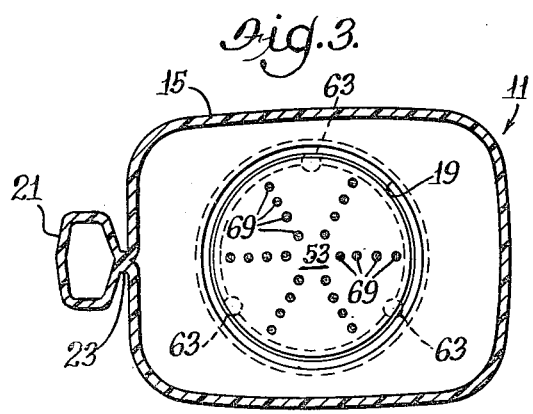
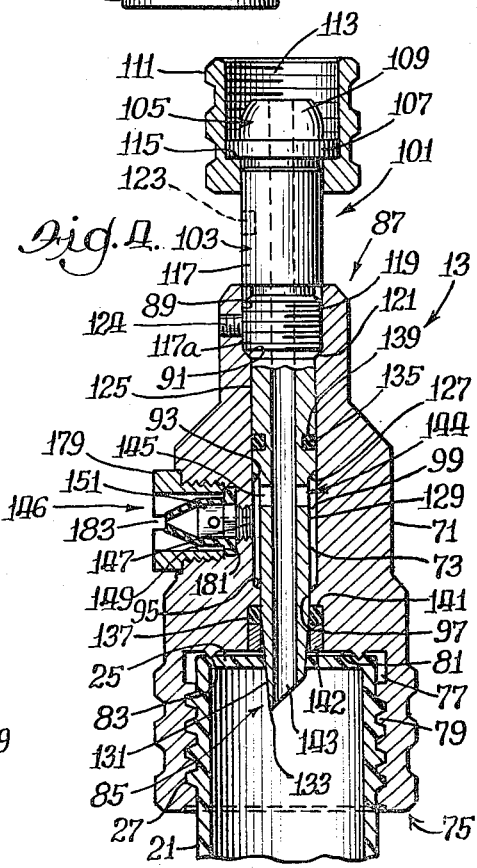
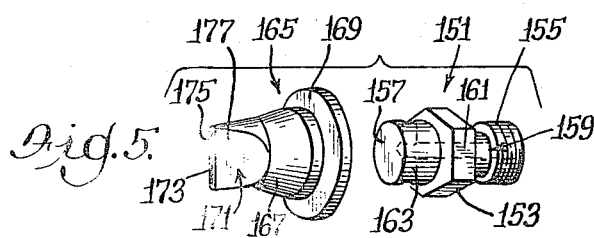

HUMIDIFIER ADAPTER WITH AUDIO RELIEF VALVE

This invention relates generally to humidifier apparatus, and more particularly to an adapter for a humidifier used in respiratory apparatus.

It is known in the treatment of persons having respiratory disorders, such as emphysema or asthma, to provide inhalation therapy through the employment of humidifiers in the respiratory apparatus. In such instances, the person affected with the disorder inhales a gas-liquid mixture from the humidifier, which is effective in moistening the gas that is passed through the humidifier and discharged therefrom in a manner to introduce the moistened gas, such as oxygen or air, into a person's respiratory system. The gas is moistened so as to prevent desiccation of the respiratory tract or membranes during treatment over a prolonged period of time. Copending applications Ser. No. 569,229, filed Apr. 18, 1975, now U.S. Pat. No. 4,061,698 and a continuation thereof, Ser. No. 763,818, filed Jan. 31, 1977, now U.S. Pat. No. 4,100,235, are assigned to the same assignee as this application and disclose humidifier-nebulizer apparatus having an adapter head that includes control valve means movable to discharge a nebulized gas-liquid mixture from the adapter head during a nebulizing mode of operation and adjustable to introduce oxygen into the liquid reservoir in a manner to effect discharge of humidified oxygen through a discharge port of the liquid reservoir of the apparatus. The humidifier of this invention is similar to that described in both the foregoing applications, but the adapter of this invention includes audible relief valve means which serves as an audible alarm to indicate an above normal pressure in the humidifier to alert an attendant of this condition.

Provision for audible signals to indicate system blockages or other causes of pressure increase are known, but the effective audio range of known devices is limited and the pressure increase may quickly pass through the audio range of the devices and continue increasing with the result that the audible device ceases to produce sound and serves only as an exit valve for gases. Thus, under conditions of abnormally high pressure, such devices could be permitted to continue in their malfunction condition without further alerting anyone as to the condition. It is desirable, therefore, to significantly increase and maximize the range in pressure over which an audible signal will be produced by the audible device to assure a time span adequate for an attendant to hear the signal and respond to it.

It is an object of this invention to provide a humidifier for respiratory apparatus employing an adapter head which includes an improved audible valve means to alert an attendant of an above normal pressure condition in the humidifier.

It is another object of this invention to provide a humidifier for respiratory apparatus which includes an audible relief valve means having an audio range effective over a flow of gas therethrough ranging from a minimum that will establish audio to approximately seven times this minimum.

Other objects and advantages of the invention will become apparent and the invention better understood by reference to the following detailed description read in conjunction with the accompanying drawing in which:

FIG. 1 is a side elevational view of a humidifier apparatus constructed in accordance with this invention and shown with all parts assembled for use;

FIG. 2 is an enlarged longitudinal sectional view of the liquid reservoir used in the apparatus of FIG. 1, the liquid reservoir being in a sealed condition prior to assembly of the adapter means thereon;

FIG. 3 is a transverse sectional view taken substantially along the line 3—3 of FIG. 2;

FIG. 4 is an enlarged longitudinal sectional view of the adapter means employed in the apparatus of FIG. 1; and FIG. 5 is an exploded view of various components utilized in the audible relief valve means of the adapter of FIGS. 1 and 4.

Referring now to the drawings, and in particular to FIG. 1, a humidifier apparatus in accordance with this invention is indicated generally at 9. This humidifier apparatus includes a respirator bottle or liquid container or reservoir, indicated generally at 11, and adapter means, indicated generally at 13. As will be described more fully below, the liquid reservoir is constructed to contain a quantity of purified or sterile liquid, such as water, and has provision for mounting the adapter means 13 thereon. In operation, the adapter means 13 is connected to a flowmeter which in turn is connected to a source of oxygen, air, or the like (not shown).

With reference to FIGS. 2 and 3, taken in conjunction with FIG. 1, the liquid reservoir 11 includes a primary or main liquid reservoir body portion 15 which terminates at its lower end in an annular wall 17. As can be seen in FIG. 3, the reservoir body portion 15 is generally rectangular in cross-sectional configuration with rounded corners. The annular wall 17 defines an opening 19 into the interior of the reservoir body 15. An upstanding filler tube 21 is preferably formed as an integral part of the reservoir body portion 15, as through a connecting web 23, and extends along the longitudinal length of the reservoir body portion 15. The upstanding filler tube 21 is connected at its lower end to the annular wall 17 in communication with the opening 19, and has a sealed upper end surface 25 which extends above the top of the reservoir body 15. An external right-hand thread 27 is formed on the outer periphery of the filler tube 21 adjacent its upper sealed end 25 to provide a threaded end upon which the adapter means 13 may be threadedly engaged. The sealed end 25 of the filler tube 21 is pierceable by a piercing element provided on the adapter means 13 as will be described more fully hereinafter.

The reservoir body 15 terminates at its upper end in a surface 29 which closes the upper end except for an opening 31 formed in the upper surface. The upper surface 29 extends upwardly in surrounding relation to the opening 31 to define a neck portion 33. The surface continues upwardly from the neck portion to terminate in an upwardly extending integral cap portion 35. The cap 35 has an upstanding cylindrical tubular extension 37 formed integrally thereon which has an upper closed end 39 and a radially outwardly extending connector nib 41. The connector nib 41 has annular ridges 43a, 43b, and 43c formed thereon which are of progressively increasing diameter and which serve to receive and retain the end of a rubber or other suitable elastomeric cannula when the humidifier is assembled into respirator apparatus.

The liquid reservoir 11 is preferably formed of a polyolefin material which lends itself to conventional blow-molding techniques. The liquid reservoir 11, as illustrated in FIG. 2, may be made by known "blowing and filling" methods and machinery. In blow-molding the liquid reservoir 11, the reservoir body 15 and the filler tube 21 are initially formed, with the sealed upper end 25 of the filler tube being formed integral during the blowing process. During the blow-molding process, a sparger, which may alternatively be termed a diffuser, and which is indicated generally at 47, is held in position between the mold halves on locating pins and molded in place.

The sparger 47 includes a lower circular, non-porous baseplate portion 49 which has an annular knurled flange 51 about which the wall 17 is formed. The sparger 47 also includes a circular planar sparger plate 53 which has a depending annular wall 55 formed integrally therewith. The lower edge of the depending wall 55 seats against an annular recessed surface 57 formed on the baseplate 49. A radial flange 59 is formed adjacent the periphery of the sparger plate 53, and the wall 17 is formed about this flange to retain the sparger plate 53 in place. The depending annular wall 55 is spaced radially inwardly from the wall 17 so as to define an annular passage 61 therebetween which is in open fluid communication with the lower end of the filler tube 21. The depending annular wall 55 has a plurality of openings 63 formed therein to provide communication between the annular passage 61, and thus the lower end of the filler tube 21, and the interior of the sparger 47. In the illustrated embodiment, three rectangular openings 63 are provided in equidistantly spaced relation about the wall 55.

After blow-forming the liquid reservoir body 15 and filler tube 21, with the sparger 47 formed in-place within the annular wall 17, a sterilized liquid, such as water 65, may be introduced through the reservoir opening 31 prior to forming the integral cap portion 35 and upstanding extension 37. After liquid is introduced into the reservoir body 15, the blowing machine forms the cap 35, the upstanding extension 37, the connecting nib 41 and a rectangular tab 65 onto the upper end 29 of the liquid reservoir adjacent the opening 31. In this manner, total sealing of the liquid 65 within the liquid reservoir 11 is accomplished. The tab 65 may subsequently be broken off from the connecting nib 41 to expose an internal orifice 67 of the connecting nib. The interior of the reservoir body 15 may then be connected through the nib 41 to the cannula 45, as shown in FIG. 1.

The sparger plate 53 of the sparger 47 has a plurality of openings 69 formed therein in a radial spoke-like pattern as shown in FIG. 3. Each of the openings 69 has an upwardly diverging frustoconical upper end 69a. When gas, such as oxygen or air, is introduced into the upper end of the filler tube 21, it pushes the liquid within the filler tube downwardly and into the reservoir body 15. The gas thus passing downwardly through the filler tube passes through the openings 63 of the sparger 47 and upwardly through the openings 69 in the sparger plate 53 where the gas reacts against the liquid surface and forms bubbles which pass upwardly through the liquid 65 for outward passage in a humidified state through the connector nib 41. It has been found that the sparger 47 provides quiet and efficient operation in carrying out its intended function.

The flat baseplate 49 of the sparger 47 cooperates with the lower end of the annular wall 17 of the reservoir body 15 to provide a surface against which a heating element may be positioned to facilitate heating of the liquid within the reservoir as desired.

Referring now to FIG. 4, taken in conjunction with FIG. 1, the adapter means 13 includes a housing or body 71 of generally cylindrical shape but having a series of steps of decreasing diameter from one end. A generally coaxial bore 73 is provided internally of the body and extends the entire length of the body. The large diameter end of the body 71, generally indicated at 75, contains a counterbore 77, the inside wall of which is provided with a thread 79 which is adapted for threaded cooperation with the thread 27 at the top of the filler tube 21 (FIG. 2). Thus, the adapter 13 is arranged for being threadedly mounted on the upper end of the filler tube 21.

A bottom 81 of the counterbore lies between the inner wall of the counterbore 77 and the wall of the bore 73. This bottom is flat except for a ring-shaped boss 83 which is V-shaped in cross section. The apex of the "V" is impressed in the top surface 25 of the filler tube when the adapter is tightly screwed onto the upstanding extension of the filler tube. This interaction between the boss 83 and the top surface 25 forms a gas-tight seal, and this seal surrounds an opening in the surface 25 caused by a piercing element 85 as the adapter is being mounted on the upper end of the filler tube.

The bore 73 in the adapter body is not of a constant diameter throughout its length. Referring to the adapter body 71 and specifically to its small diameter end, which is designated 87, there is a large diameter portion 89 of the coaxial bore 73. This portion 89 is threaded on its inner wall and terminates inwardly at a frustoconical shoulder or stop surface 91 at which point the diameter of the bore steps to a mid diameter portion 93. This mid diameter portion has a smaller diameter than the portion 89 and extends from the inner end of the shoulder 91 to another step in bore diameter at a further shoulder 95. Adjacent the shoulder 95 is a small diameter portion 97 of the bore 73. This small diameter portion 97 terminates adjacent the counterbore bottom 81, whereafter the diameter substantially increases to the extent of the counterbore 77.

The wall of the mid diameter portion 93 defines the outer wall of a pressure chamber 99, which, as will be described hereinafter, is an important feature of this invention.

A spike member 101 is provided in a seated, snug relation longitudinally of the body 71 in the coaxial bore 73 and extends from the small diameter end 87 of the body 71 through all three bore portions, i.e., the large diameter portion 89, the mid diameter portion 93, and the small diameter portion 97, and finally into the counterbore 77. In the illustrated embodiment, this spike member 101 includes a generally tubular body 103 and a connector head 105. The head includes a lock collar flange 107 and a spherical end 109 adapted to mate with, for example, a seal in a flowmeter, represented at 112. A separate nut 111, generally cylindrical in shape, fits over the head 105 and is used for attaching to a standard thread on the flowmeter 112 (FIG. 1) in gas-tight relation to the spike head 105 by means of an internal thread 113 and a locking shoulder 115. Thus, a suitable end fitting (not shown) of the flowmeter 112 is forced into a sealed relation with the top side of the collar 107 as the shoulder 115 abuts the underside of the collar 107 and the nut is screwed tightly onto the gas tube end fitting. When this connection is complete, the rounded connector insert portion 109 fits in a snug relation in the fitting.

The nut 111 may include a suitable gripping surface, such as a knurl to enhance hand connection of the parts.

The tubular body 103 of the spike 101 in the direction away from the head 105 includes at least the same number of stepped diameter portions as the coaxial bore 73 of the adapter body 71. Thus there is, in the illustrated embodiment, a large diameter portion 117 of the tubular body 103 that extends between, and separates, the connector head 105 and the upper end 87 of the adapter body 71. A portion 117a of the large diameter portion is provided with a thread 119 that is adapted to threadedly cooperate with the threaded interior wall of the large diameter portion 89 of the bore 73. The lead end of the threaded portion 117a terminates in a frustoconical shoulder 121 that opposes and complements the shoulder or stop surface 91 of the adapter body 71. When these two surfaces meet, the inward movement of the spike member 101 is stopped and a seated relation then exists between the spike member and the adapter body. A detent 123 for a torque tool, such as a spanner wrench, is provided in the outer surface of the large diameter portion 117 to assist in inserting or removing the spike member 101. A securing means, such as a socket type set screw 124 (FIG. 1) is located in the small diameter end 87 of the adapter so as to be tightenable against the thread 119 to prevent unwanted rotation of the spike member 101 after it is properly seated.

There is also a mid diameter portion 125 of the tubular body 103 that partially coincides with the mid diameter portion 93 of the bore 73. It does not, however, extend all the way to the shoulder 95, but terminates in a stepped or beveled surface 127 that leads to a small diameter portion 129 of the tubular body 103. This small diameter portion 129 terminates at its lead end in the piercing element 85, which is provided with both a taper 131 and a point 133.

As mentioned previously, the wall of the mid diameter portion 93 of the bore 73 defines the outer wall of the pressure chamber 99. This chamber is otherwise generally defined by the stepped or beveled surface 127 at one end, the surface of the small diameter portion 129 of the spike member 101 as the inner wall, and the shoulder 95 of the adapter body 71 at the other end in addition to the wall of the mid diameter portion 93 of the bore as the outer wall.

The ends of the chamber 99, however, are more specifically defined by first and second seal means between the tubular body 103 and the bore 73. In the illustrated embodiment these seal means are in the form of "O" rings 135 and 137, the "O" ring 135 being located in a ring groove 139 in the mid diameter portion 125 of the spike member 101 and the "O" ring 137 being located in a ring groove 141 in the small diameter portion 97 of the bore 73. The ring groove 141 may be made in any suitable manner in accordance with generally known machining principles. One method is to form a counterbore in the bore 73 to the desired depth, the flat bottom of the new counterbore being the inner wall of the ring groove 141. The "O" ring 137 is then inserted. Next, a ring insert 142 is press-fit into position to fill the balance of this added counterbore and form the other wall of the groove 141 on one side and a substantially flush surface with the bottom 81 on the other.

Accordingly, in this illustrated embodiment, one seal means is integral with the spike member and the other seal means is integral with the adapter body, but both are compressed by their respective opposing parts during assembly to form a gas-tight seal at both ends of the compression chamber 99. Although the seal means just described are proposed for either end of the chamber, it should be recognized that other seal means could be utilized as long as the devices can be readily assembled and disassembled and proper seals are established between the spike member and the wall of the bore in the adapter body to define the ends of the compression chamber 99.

The tubular body 103 of the spike member defines a longitudinal internal passage 143, which may be in the form of a constant-diameter bore. This passage serves as a conduit for the pressurized gas through the adapter 13 between the gas tube and the filler tube 21 to allow the gas to pass through the humidifier 9 for moistening before discharge into the cannula 45.

Two port means 144 and 146 are provided in communication with the pressure chamber 99. A first of these port means 144 includes a port 145 through the wall of the tubular body 103 of the spike member 101 in the zone of the small diameter portion 129 of the spike. Axially, this first port 145 is located near the step in diameter from the mid diameter portion 125 of the spike. This first port establishes communication between the gas passage 143 and the pressure chamber 99. It may be formed in any suitable manner, such as by drilling into the wall of the spike member 101 completely through a diameter of the spike at right angles to its axis.

The second of these is port means 146 and includes a port 147 through the wall of the adapter body in the zone of the mid diameter portion 93 of the bore 73. Axially, this second port 147 is displaced from the location of the first port 145 so that they are not opposite one another. This second port establishes communication between the pressure chamber 99 and the outside atmosphere. It, likewise, is formed in any suitable manner, such as by drilling, but the drilling is limited to the portion of the wall on one side of the axis only, i.e., it does not extend completely through the diameter of the adapter. A counterbore 149 extends inwardly from the outer cylindrical surface of the adapter body to a depth approximating three-quarters the wall thickness. The walls of both the port 147 and the counterbore 149 are threaded for purposes described hereinafter.

In this illustrated embodiment, the port means 146 includes three parts that are applied in the combination port 147 and counterbore 149. With reference to FIG. 5, the first of these parts is a pressure bushing 151, which includes a hexagon-shaped body 153 from which depends a threaded shank 155. On the other side of the body 153 from the shank is a discharge head 157. A "T" shaped passage 159 is provided internally of the pressure bushing 151. The longitudinal portion of the "T" shaped passage is designated at 161 and is substantially coaxial with the bushing. This longitudinal portion 161 extends from the shank end into the head 157, but not completely through the head. Instead, a transverse portion 163 extends through a diameter of the head 157 and intersects the longitudinal portion 161 internally of the head and establishes communication with the longitudinal portion. Thus, gas passing into the longitudinal portion from the shank end is discharged laterally of the bushing, i.e., out both sides of the head 157.

The shank 155 and the port 147 are both threaded to cooperate with each other, and the bushing 151 is inserted in the port by screwing the bushing, shank end first, into the port by a suitable tool applied to the hexagon-shaped body 153 of the bushing. When completely inserted, the body 153 will be tight against the bottom of the counterbore 149.

The next of the three parts of the port means 146 is a duck bill valve 165, which includes a hollow body 167, a mounting flange 169, a duck bill head 171 and a slit 173 defined between two opposing sides or wall portions 173 and 175 of the duck bill 171. The hollow body 167 is of sufficient dimensions to fit over both the discharge head 157 and the hexagon-shaped body 153. The outer diameter of the flange 169 is slightly smaller than the diameter of the counterbore 149 so that the flange rests flatly against the bottom surface of the counterbore 149 when the bushing 151 and the valve 165 are installed. The duck bill discharge head 171 extends above the head 157 of the bushing in the installed condition. The two opposing tapered sides or wall portions 175 and 177 of the duck bill 171 are flexible and vibratable and converge to an apex where the two sides define the slit 173 between them. Normally this slit is closed as the two opposing sides lie flat against each other at the apex. When there is gas pressure, however, these portions separate and allow a gas discharge through the slit. These wall portions are adapted to vibrate and produce an audible signal when gas flows between them.

Referring once again to FIGS. 1 and 4, the third part of the port means 146 in the adapter body 71 is a valve screw 179. This valve screw has a generally cylindrical body which is threaded on its outer surface in a manner to cooperate with the threaded wall of the counterbore 149. The inside of the valve screw is hollow and surrounds the duck bill valve 165 when the valve screw is tightly in place. The valve screw includes a leading face 181 which is applied against the flange 169 of the duck bill valve 165 both to secure the position of the valve 165 and to form a seal between the flange and the bottom surface of the counterbore 149. A screwdriver slot 183 is provided to assist in inserting and removing the valve screw 179.

The adapter means illustrated in FIG. 4 is preferably metallic and is made, for example, by machining suitable material, such as brass. All such brass parts are then preferably covered with a chrome plate. The pressure bushing 151 may be finished with a bright nickel coat. The set screw 124 may be stainless steel. The two "O" rings 135 and 137 and the duck bill valve 165 are preferably made from a silicone rubber having the ability of withstanding temperatures normally experienced in a steam autoclave, such as 250° F. to 275° F. for thirty minutes. Preferably, the material will withstand temperatures of 400° F. or more. An example of such material is a 45 durometer methyl-vinyl siloxane polymar processed for use in external medical equipment. This construction allows the adapter means 13 to be sterilized as needed.

In operation, it is contemplated that the humidifier apparatus 9 as described herein will be utilized as a part of respiratory apparatus to humidify a gas in inhalation therapy. If pressure rises above normal in the respirator bottle or liquid reservoir 11, no matter what the cause, the adaptor means 13 will serve as an audible alarm to attract the attention of an attendant who can inspect the apparatus and remove the cause of the high pressure. If the pressure in the respirator bottle is high as a result of high pressure from the gas source, globules of water may form and exit the humidifier apparatus and enter the lungs of the patient. On the other hand, if high pressure in the respirator bottle is the result, for example, of an occlusion in the outgoing line, whether by pinching of the line or other, humidified gas may not reach the lungs at all. In either situation, the result is a malfunction and an attendant should make an appropriate remedial adjustment.

Accordingly, gas flow exceeding a predetermined pressure is audibly vented to the atmosphere through the duck bill valve 165. The pressure chamber 99 acts as a buffer to smooth the outward flow of gas and facilitate the audio vibratory action of the opposing walls 175 and 177 of the valve 165. In a device constructed in accordance with the illustrated embodiment, the audio range has been found to be effective from about 0.07 cfm to about 0.5 cfm.

As an example, one adapter means has been constructed in which the adapter body 71 is approximately two and one-half inches long and has a mid diameter bore portion 93 of approximately 0.32 inch. The small diameter portion 129 of the spike member 101, on the other hand, has a diameter of approximately 0.22 inch, allowing a side wall to side wall distance in the pressure chamber 99 of approximately 0.05 inch. The length of the chamber as measured between the stepped surface 127 of the spike 101 and the stepped surface or shoulder 95 of the adapter body is approximately 0.47 inch. The seal means that seal these ends of the chamber, of course, are axially spaced outwardly of these two stepped surfaces as can be seen of the drawing (FIG. 4). The first port 145 in the spike 101 has a diameter of 0.046 inch, and the second port 147 in the wall of the adapter body 71 consists of clearance hole for a 5–40 tap. An axial distance of about 0.047 inch separates the centers of these two ports. The material for the adapter body 71, the spike member 101, the nut 111, and the valve screw 179 is chrome plated brass. The set screw 124 is a socket type made of stainless steel. The pressure bushing 151 is brass with a bright nickel finish. The duck bill valve 165 is made of rubber having the same characteristics as described earlier in connection with the O-rings 135 and 137. It is approximately 0.3 inch in diameter at the flange 169 end and is approximately 0.285 inches in length. The outer diameter of the hollow body 167 is approximately 0.2 inch.

Generally, the gas flow through the adapter means 13 and the bottle 11 to the patient ranges from approximately 2 liters per minute to approximately 15 liters per minute, that is to say, from approximately 0.07 cfm to approximately 0.53 cfm. In the aforedescribed construction, an internal pressure build of 3 to 3.5 psig will cause an outward flow of about 0.07 cfm through the duck bill valve 165. Such pressure buildup might result, for example, from a kink or other obstruction in the cannula 45 leading to the patient. In accordance with this invention, the duck bill valve 165 is effective to respond to such low gas flow of about 0.07 cfm by an audible vibration of the opposing wall portions 175 and 177. This audible vibration of these opposing walls continues until the flow of gas outwardly of the duck bill valve exceeds about 0.5 cfm. In terms of liters per minutes, this means that the valve audibly vibrates at gas flow rates therethrough within a range of from 2 to 15 liters per minute. At gas flow rates exceeding 15 liters per minute, the opposing wall portions 175 and 177 remain separated without audibly vibrating as the gas flows therebetween. The flow of 15 liters per minute (about 0.53 cfm) at the upper end of the audible range results from a pressure in the respirator bottle 11 of about 6.5 psig.

Thus, the audio vibrations are produced in the duck bill valve 165 at internal pressures of 3 to 6.5 psig at gas flow rates of 2 to 15 liters per minute. In combination with the pressure chamber 99, a sustained, audible signal will be provided to alert an attendant to the fault condition so that corrective action can be taken and the patient can again receive moistened gas from the system.

In summary, there has been shown and described a humidifier adapter 13 for mounting on an engageable portion of a container or liquid reservoir 11 over a pierceable sealed surface 25 of the container. A supply of purified or sterile water 65 is sealed in the container. The adapter also connects a pressurized gas tube 112 to the container for introducing gas into the supply of water to moisten or humidify the gas. The adapter 13 includes a housing or body 71 having means at one end for engaging the container and a bore axially extending through the housing. A spike member 101 is provided and inserted within the housing 71. This spike member has a generally tubular body with one pointed end. The outer surface diameter of a portion of this tubular body is sufficiently less than the adjacent bore diameter in a corresponding axial portion of the bore so as to define therebetween a pressure chamber 99. The ends of the pressure chamber 99 are sealed by first and second seal means between the spike member and the wall of the bore that are axially spaced apart from each other. A first port means 144 is provided in the tubular body of the spike member 101 and establishes communication between the inside passage 143 of the spike member, through which gas enters the container, and the pressure chamber 99. A second port means 146 is provided in the housing wall and is located to establish communication between the pressure chamber 99 and the outside atmosphere. The centers of these ports are not in line but are axially spaced apart from each other. Both ports, however, are located intermediate the first and second seal means. An audible relief valve means including valve 165 is located in the second port means 146 and effects audible pressure relief of the pressure chamber under above normal pressure conditions. The illustrated audible relief valve means has an effective audible range from the minimum flow that establishes sound to approximately seven times such minimum flow.

Although the invention has been described in connection with a preferred embodiment, alternatives, modifications, and variations may be apparent to those skilled in the art in view of the foregoing description. Accordingly, it is intended to embrace all such alternatives, modifications, and variations as fall within the spirit and scope of the appended claims.

What is claimed is:

1. A humidifier adapter for mounting on an engageable portion of a container over a pierceable seal thereon sealing therein a supply of sterile water, and to be connected to a pressurized gas tube for introducing gas into the supply of water to moisten the gas, said adapter comprising:
    a housing having means at one end thereof for engaging the container;
    an axial bore through said housing;
    a spike member for assembly within said housing, said spike member having a tubular body defining a gas passage therein and having one pointed end and being insertable in said bore, the outer surface diameter of said tubular body being substantially less, at least along an axial portion thereof, than the adjacent bore diameter of said housing so as to define a pressure chamber therebetween when said spike member is in inserted relation within said housing;
    first and second seal means between said tubular body and the wall of said bore axially spaced apart from each other to form the ends of said pressure chamber;
    first port means in the tubular body of said spike member establishing communication between the internal gas passage of said tubular body and the pressure chamber;
    second port means in the housing wall establishing communication between the pressure chamber and the outside atmosphere, said second port means being located with respect to said first port means such that their centers are spaced apart along the axis of said housing, both said port means being located intermediate said first and second seal means that form the ends of the chamber; and
    audible relief valve means located in said second port means to effect audible pressure relief of the pressure chamber under above normal pressure conditions.

2. An adapter in accordance with claim 1 wherein said first seal means is an "O" ring contained in a groove in said spike member and said second seal means is an "O" ring contained in a groove in said housing wall.

3. An adapter in accordance with claim 1 wherein said first and second seal means are "O" rings made of a silicone rubber capable of withstanding temperatures normally experienced in a steam autoclave.

4. An adapter in accordance with claim 1 wherein said housing and said spike member are made of brass having chrome plate surfaces.

5. An adapter in accordance with claim 1 wherein audible relief valve means includes an audible duck bill type flexible valve made of a silicone rubber capable of withstanding temperatures normally experienced in a steam autoclave.

6. An adapter in accordance with claim 5 wherein said duck bill valve has an audio range effective with gas flows therethrough of from 2 to 15 liters per minute.

* * * * *